United States Patent [19]

Ishii et al.

[11] Patent Number: 4,683,341
[45] Date of Patent: Jul. 28, 1987

[54] OPTICAL RESOLUTION OF OXYCYCLOPENTENONE

[75] Inventors: Kunio Ishii, Hasuda; Tohru Shibata, Himeji, both of Japan

[73] Assignee: Daicel Chemical Industries, Ltd., Sakai, Japan

[21] Appl. No.: 808,593

[22] Filed: Dec. 12, 1985

[30] Foreign Application Priority Data

Dec. 19, 1984 [JP] Japan .................. 59-266294

[51] Int. Cl.$^4$ ............................................. C07C 45/79
[52] U.S. Cl. ................................... 568/366; 568/324; 560/104; 560/105; 560/106; 560/218; 560/248
[58] Field of Search ............... 568/360, 338, 366, 324; 560/104, 105, 106, 218, 248

[56] References Cited

FOREIGN PATENT DOCUMENTS 0153653 9/1985 European Pat. Off. ............ 568/366

OTHER PUBLICATIONS

Sumitomo, Chem. Abst., vol. 100 #16994w (1984).
Sumitomo, Chem. Abst., vol. 98, #27097x (1983).
Sumitomo, Chem. Abst., vol. 100 #163020z (1984).

*Primary Examiner*—James H. Reamer
*Attorney, Agent, or Firm*—Flynn, Thiel, Boutell & Tanis

[57] ABSTRACT

The optical resolution of an enantiomer mixture of oxycyclopentenone or a derivative thereof is conducted with a polysaccharide derivative.

10 Claims, 1 Drawing Figure

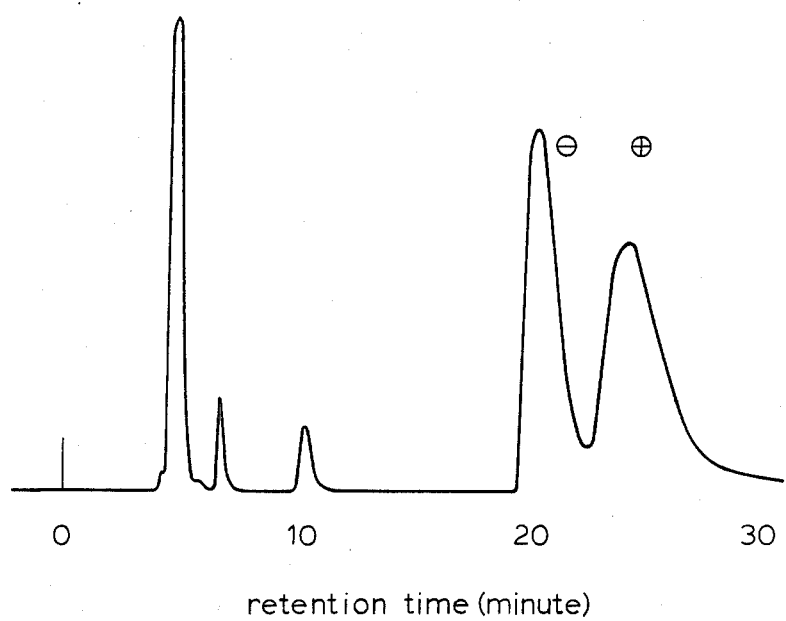

OPTICAL RESOLUTION OF OXYCYCLOPENTENONE

The invention relates to optical resolution of oxycyclopentenone. The method of the invention extends to treatment of a derivative of oxycyclopentenone.

Since one enantiomer of an asymmetric compound differs from the other in the action on a living body, the optical resolution of an enantiomer mixture and an asymmetric synthesis have been have important in organic chemistry.

As the conventional process for obtaining optically active compounds, there can be mentioned asymmetric synthesis, optical resolution by way of a diastereomer, and biochemical synthesis using an enzyme or microorganism. The asymmetric synthesis process is defective in that an intended compound having a high optical activity cannot be obtained, and the process by way of a diasteromer is disadvantageous in that formation of a diastereomer itself is difficult and equimolar amounts of different optically active compounds are necessary. Furthermore, the biochemical process is defective in that it is difficult to find an appropriate enzyme or microorganism.

With compounds represented by the general formula (I) set forth hereinbelow, various chemical conversions are possible through addition reaction to the double bond of the 5-membered ring, and therefore, these compounds are important intermediates for the synthesis of organic compounds having a 5-membered ring. For example, a compound (A) ($R^1=R^2=H$, $X=OH$) is a starting material of various prostanoids which attract attention as medicines. See Stork and M. Isobe, J. Amer. Chem. Soc., 97, 6260 (1975) and R. Noyori and M. Suzuki, Angew. Chem. Int. Ed. Engl. 23, (1984) 84. Since the desired prostanoids are optically active, the optically active compound (A) is preferably used as the starting substance. No method for isolating the compound (A) on an industrial basis has been found yet. Similarly in the case of a compound (B) ($R^1=CH_2=CH—CH_2—$, $R^2=CH_3$, $X=OH$) or compound (C) ($R^1=CH=CH—CH=CH—CH_2—$, $R^2=CH_3$, $X=OH$), which constitutes a skeleton of a pyrethroid type insecticide, complicated steps are necessary for the optical resolution. Accordingly, if oxycyclopentenone and its derivatives, which are intermediates for the synthesis of various biologically active substances, can be directly optically resolved according to a process that can be easily carried out on an industrial scale, great contributions will be made to the art.

SUMMARY OF THE INVENTION

The invention method for the optical resolution of oxycyclopentenone or a derivative thereof having the below shown formula comprises the step of treating an enantiomer mixture of the oxycyclopentenone or the derivative with a resolving agent comprising a polysaccharide derivative to perform the optical resolution.

General formula (I) is as follows:

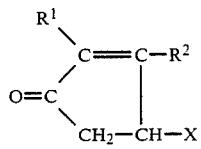

in which R1 is hydrogen or an alkyl having 1 to 10 carbon atoms, which may contain an aromatic group, R2 is hydrogen or an alkyl having 1 to 10 carbon atoms, which may contain an aromatic group, or an unsaturated aliphatic group having 1 to 10 carbon atoms, which may contain an aromatic group, and X is hydroxyl or —OR3, R3 being a protective group for hydroxyl group.

The protective group to use as R3 in the invention method may be any group which is useful as a protective group, preferably including an acyl group, α,α-dimethylbenzyl, α-alkoxyalkyl, triaryl-methyl and silyl.

In the formula, X may be defined to be OH, OCOR4 or OR5 in which R4 is an alkyl group having 1 to 10 carbon atoms, which may contain an aromatic group, an unsaturated aliphatic group having 1 to 10 carbon atoms, which may contain an aromatic group, or an aromatic group having up to 10 carbon atoms and R5 is an alkyl group having 1 to 10 carbon atoms, which may contain an aromatic group, or an unsaturated aliphatic group having 1 to 10 carbon atoms, which may contain an aromatic group.

As specific examples of $R_1$, there can be mentioned H, $CH_2=CH—CH_2—$ and $CH_2=CH—CH=CH—CH_2—$ and as specific examples of $R_2$, there can be mentioned H and $CH_3$. X is a group capable of reacting easily with the resolving agent. For example, there can be mentioned OH, $OCOC_6H_5$, substituted $OCOC_6H_5$, $OCOCH=CHC_6H_5$, substituted $OCOCH=CHC_6H_5$, and $OCH_2C_6H_5$ and substituted $OCH_2C_6H_5$. The groups OH and $OCOC_6H_5$ are especially preferred.

(Resolving Agent)

The resolving agent used in the present invention comprises a polysaccharide or its derivative as an effective component. Any of synthetic polysaccharides, natural polysaccharides and modified natural polysaccharides may be used as far as it is optically active. Homoglycans having a high regularity are preferred and it is preferred that the bonding mode be constant. Furthermore, it is preferred that a polysaccharide having a high purity be easily obtained. As preferred examples of the polysaccharide, there can be mentioned cellulose, amylose, β-1,4-chitosan, chitin β-1,4-mannan, β-1,4-xylan, inulin, α-1,3-glucan and β-1,3-glucan. In polysaccharide derivatives, a part or all, preferably at least 85%, of hydrogen atoms on hydroxyl groups of the foregoing polysaccharides are substituted by other atomic groups such as

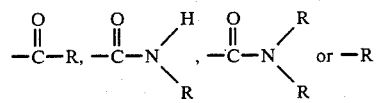

wherein R stands for an aliphatic group having 1 to 3 carbon atoms, an alicyclic group having 3 to 8 carbon atoms or an aromatic or heteroaromatic group having 4 to 20 carbon atoms, which may have a substituent. These derivatives can be easily obtained by various known reactions. These polysaccharides and their derivatives are especially suitable for the chromatographic separation carried out on an industrial scale because starting materials are easily available and the stability is high.

According to the optical resolution process of the present invention, if an appropriate resolving agent is selected from the polysaccharide and a derivative thereof defined above, oxycyclopentenone and a derivative thereof can be optically resolved.

The preparation of the resolving agent used in the present invention will now be described.

When the liquid or gas chromatography is adopted, the polysaccharide or its derivative is packed in a column directly or after it has been supported on a carrier, or it is applied on a capillary column.

Since a granular resolving agent is preferred for the chromatographic separation, when the polysaccharide or its derivative is used as the resolving agent, it is preferred that the polysaccharide or its derivative be pulverized or formed into beads. The particle size is variable according to the size of the column or plate used, but it is ordinarily 1 µm to 10 mm and preferably 1 µm to 300 µm. It is preferred that the particles be porous.

In order to improve the pressure resistance of the resolving agent, prevent swelling or shrinkage by the solvent substitution and increase the number of theoretical stages, it is preferred that the polysaccharide or its derivative be supported on a carrier. The size of the carrier is variable according to the size of the column or plate used, but it is ordinarily 1 µm to 10 mm and preferably 1 µm to 300 µm. It is preferred that the carrier be porous, and the average pore size is 10 Å to 100 µm, preferably to 50 Å to 10000 Å. The amount of the polysacharride or its derivative held on the carrier is ordinarily 1 to 100% by weight and preferably 5 to 50% by weight based on the carrier.

Either a chemical method or a physical method may be used to support a polysaccharide or a derivative thereof on a carrier. As the physical method, there can be mentioned a method in which a polysaccharide or its derivative is dissolved in a solvent, the solution is sufficiently mixed with a carrier and the solvent is distilled off under reduced pressure or by heating or by an air current, and a method in which a polysaccharide or its derivative is dissolved in a solvent, the solution is sufficiently mixed with a carrier and the mixture is stirred and dispersed in a liquid having no compatibility with the solvent to diffuse the solvent. A heat treatment or the like may be performed so as to crystallize the polysaccharide or its derivative thus supported on the carrier. Moreover, there may be adopted a method in which a small amount of a solvent is added to swell or dissolve the polysaccharide or its derivative and the solvent is then distilled off to change the supported state and the resolving characteristics.

A porous organic carrier and a porous inorganic carrier can be used, and a porous inorganic carrier is preferable. As preferred examples of the porous organic carrier, there can be mentioned polymeric substances such as polystyrene, polyacrylamide and polyacrylate, and as preferred examples of the porous inorganic carrier, there can be mentioned synthetic and natural substances such as silica, alumina, magnesia, titanium oxide, glass, silicate and kaolin. A surface treatment may be carried out so as to improve the affinity with the polysaccharide or its derivative. As the surface treatment, there can be mentioned a silane treatment using an organic silane compound and a plasma polymerization surface treatment.

When a polysaccharide or its derivative is used for the optical resolution, even in chemically identical derivatives, the resolution characteristics differ according to the physical properties such as the molecular weight, the degree of crystallization and the orientation. Accordingly, the polysaccharide or its derivative may be subjected to a physical or chemical treatment such as a heat treatment or an etching treatment after a shape suitable for the intended use has been given or during the step of giving a shape suitable for the intended use.

In the case where the thin layer chromatography is carried out, a layer having a thickness of 0.1 to 100 mm, which is composed of particles of the resolving agent of the present invention having a size of about 0.1 µm to about 0.1 mm and, optionally, a small amount of a binder, is formed on a supporting plate.

As the means for obtaining an optically active compound by using the above-mentioned resolving agent in the present invention, there can be mentioned chromatographical processes such as gas chromatography, liquid chromatography and thin layer chromatography.

Any solvent may be used in the liquid chromatography and the thin layer chromatography in addition to a solvent for polysaccharide or a derivative thereof. If the resolving agent is chemically bonded to the carrier or is insolubilized by crosslinking, any liquids other than reactive liquids may be used without any limitation. Of course, the resolution characteristics of a compound or an optical isomer vary according to the kind of the developing solvent, so that it is desirable to examine various solvents.

The reason why the optical resolution of a compound represented by the general formula (I) is effectively attained according to the process of the present invention has not been elucidated. However, it is confirmed that the carboxyl group interacts with the polysaccharide derivative as the resolving agent, and it is believed that the specific structure in which this carbonyl group is coupled with a hydroxyl, alkoxy or acyl group as another interacting group through the cyclopentenone ring having a very rigid steric structure makes important contributions to the attainment of high optical resolution.

According to the present invention having the above-mentioned constitution, an optically active isomer of a compound represented by the general formula (I), which is an important industrial material, can be easily obtained by using a cheap starting material and adopting a simple chemical conversion and a chromatographic technique. The invention makes great contributions to the synthesis of many further optically active compounds from the above listed, optically active compounds. That is, the invention provides useful intermediates.

BRIEF DESCRIPTION OF THE DRAWING

The drawing is a chromatogram obtained by liquid chromatography.

The present invention will now be described in detail with reference to the following examples that by no means limit the scope of the invention.

Incidentally, as the liquid chromatography column, a stainless column having a length of 25 cm and an inner diameter of 0.46 cm was used. It was charged with a filler which was comprised of silica gel treated with diphenylsilane and about 22 wt.% of cellulose triacetate supported on the silica gel.

The optical isomer eluted out was detected with a ultraviolet detector, Shimazu SPD-II, a tradename of Shimazu, a differential refractometer, Shodex RI SE 31, a tradename of Showa Denko, and a polarimeter, DIP 181, tradename of Japan Spectrosocpic Co., Ltd.

EXAMPLE 1

A compound 4-hydroxycyclopentenone ($R^1=R^2=H$, $X=OH$) was developed with an elutant comprising hexane and 2-propanol (9:1) by using the cellulose triacetate column, and the obtained chromatogram and the optical rotatory power of each peak are shown in the drawing. The analysis temperature was 20° C., the flow rate was 0.5 mliter/min. When an ultraviolet absorption at 210 nm was used for the detection, 25 μg of the sample was injected, and when the differential refractometer was used, about 0.5 mg of the sample was injected.

A volume ratio (k') and a separation coefficient ($\alpha$) are calculated using the below listed respective equations.

$$\text{volume ratio } (k') = \frac{\text{(retention time of enantiomer mixture)} - \text{(dead time)}}{\text{(dead time)}}$$

$$\text{separation coefficient } (\alpha) = \frac{\text{(volume ratio of more strongly absorbed enantiomer)}}{\text{(volume ratio of less strongly absorbed enantiomer)}}$$

In this example, $k'1=4.44$, $k'2=5,48$ and $\alpha=1.23$.

EXAMPLES 2

When a compound 4-acetoxycyclopentenone ($R^1=R^2=H$, $X=OCOCH_3$) was developed under the same conditions as described in Example 1, partial resolution was observed, and an enantiomer having a negative optical rotation was first eluted.

EXAMPLE 3

A resolving agent was prepared by filling a stainless column having an inner diameter of 0.46 cm and a length of 25 cm with a resolving agent comprising 22 percent by weight of cellulose trisphenylcarbamate and silica gel, Chrospher Si 1000, a tradename of Merck, treated with diphenyldimethylsilane. 4-oxycyclopentenone was examined in the optical resolution with the resolving agent, using a solvent mixture of hexane and 2-propanol at a mixing volume ratio of 2:1, at a flow rate of 0.5 ml per min., at a column temperature of 20° C. As a result, $k'1$ was 8.54, $k'2$ was 9.21 and $\alpha$ was 1.08. treating silica gel with diphenylsilane.

The embodiments of the invention in which an exclusive priviliege or property is claimed are defined as follows:

1. A method for chromatographically separating a mixture of optically active enantiomers having the formula

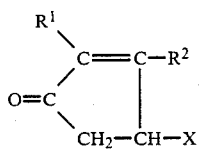

in which $R^1$ is hydrogen, alkyl having 1 to 10 carbons or alkyl having 1 to 10 carbon atoms and containing an aromatic group; $R^2$ is hydrogen, alkyl having 1 to 10 carbon atoms, alkyl having 1 to 10 carbon atoms and containing an aromatic group, unsaturated aliphatic group having 1 to 10 carbon atoms or unsaturated aliphatic group having 1 to 10 carbon atoms and containing an aromatic group; and X is OH or $OR^3$, wherein $R^3$ is a protective group for protecting a hydroxyl group, which comprises the steps of: under chromatographic separation conditions, passing said mixture with an eluant therefor into contact with a resolving agent comprising an optically active polysaccharide or a derivative thereof in which at least part of the hydrogen atoms on the hydrodoxyl groups of the polysaccharide are replaced by a member selected from the group consisting of

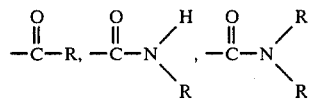

and R, wherein R is an aliphatic group having 1 to 3 carbon atoms, an alicyclic group having 3 to 8 carbon atoms, an aromatic group having 4 to 20 carbon atoms, or a heteroaromatic group having 4 to 20 carbon atoms.

2. A method as claimed in claim 1, in which in the formula R1 and R2 are each hydrogen and X is OH.

3. A method as claimed in claim 1, in which in the formula R1 and R2 are each hydrogen and X is —OR3.

4. A method as claimed in claim 1 in which said eluant is a liquid solvent for said mixture and said resolving agent is cellulose triacetate supported on silica gel.

5. A method as claimed in claim 1 in which said eluant is a liquid solvent for said mixture and said resolving agent is cellulose trisphenyl carbamate supported on silica gel.

6. A method as claimed in claim 1 in which $R^3$ is selected from the group consisting of acyl groups, $\alpha,\alpha$-dimethylbenzyl, $\alpha$-alkoxyalkyl, triarylmethyl and silyl.

7. A method as claimed in claim 1 in which $R^3$ is $COR^4$ or $R^5$, wherein $R^4$ is alkyl having 1 to 10 carbon atoms, alkyl having 1 to 10 carbon atoms and containing an aromatic group, an unsaturated aliphatic group having 1 to 10 carbon atoms, an unsaturated aliphatic group having 1 to 10 carbon atoms and containing an aromatic group, or an aromatic group having up to 10 carbon atoms, and $R^5$ is alkyl having 1 to 10 carbon atoms, alkyl having 1 to 10 carbon atoms and containing an aromatic group, an unsaturated aliphatic group having 1 to 10 carbon atoms, or an unsaturated aliphatic group having 1 to 10 carbon atoms and containing an aromatic group.

8. A method as claimed in claim 1 in which X is OH, $OCOC_6H_5$, $OCOCH=CHC_6H_5$ or $OCH_2CH_6H_5$.

9. A method as claimed in claim 1 in which said polysaccharide is selected from the group consisting of cellulose, amylose, $\beta$-1,4-chitosan, chitin, $\beta$-1,4-mannan, $\beta$-1,4-xylan, inulin, $\alpha$-1,3-glucan and $\beta$-1,3-glucan.

10. A method as claimed in claim 1 in which said resolving agent is a derivative of an optically active polysaccharide in which at least 85% of the hydrogen atoms on the hydroxyl groups have been replaced by

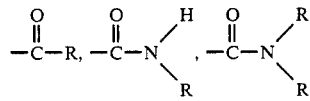

or R.

* * * * *

UNITED STATES PATENT AND TRADEMARK OFFICE
CERTIFICATE OF CORRECTION

PATENT NO. : 4 683 341
DATED : July 28, 1987
INVENTOR(S) : Kunio ISHII et al

It is certified that error appears in the above-identified patent and that said Letters Patent is hereby corrected as shown below:

Column 6, line 52; change "or $OCH_2CH_6H_5$" to ---or $OCH_2C_6H_5$---.

Signed and Sealed this

Twenty-third Day of February, 1988

Attest:

DONALD J. QUIGG

Attesting Officer — Commissioner of Patents and Trademarks